United States Patent
Abou-Krisha et al.

(10) Patent No.: US 12,358,943 B1
(45) Date of Patent: Jul. 15, 2025

(54) METHOD OF SYNTHESIZING TESTOSTERONE-BASED THIAZOLIDINONE DERIVATIVES

(71) Applicant: IMAM MOHAMMAD IBN SAUD ISLAMIC UNIVERSITY, Riyadh (SA)

(72) Inventors: Mortaga Mohamed M. Abou-Krisha, Riyadh (SA); Abdulrahman G. Alhamzani, Riyadh (SA); Al-Hassan S. Mahdy, Shenzhen (CN); Ehab Abdelhamed Abdelrahman Ahmed, Riyadh (SA); Mohamed Abd-Elsabour, Luxor (EG); Abdullah A. Aldakhil, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 19/044,731

(22) Filed: Feb. 4, 2025

(51) Int. Cl.
*A01N 45/00* (2006.01)
*A01P 1/00* (2006.01)
*A01P 3/00* (2006.01)
*C07J 43/00* (2006.01)

(52) U.S. Cl.
CPC .......... *C07J 43/003* (2013.01); *A01N 45/00* (2013.01); *A01P 1/00* (2021.08); *A01P 3/00* (2021.08)

(58) Field of Classification Search
CPC ......... C07J 43/003; A01N 45/00; A01P 1/00; A01P 3/00
See application file for complete search history.

(56) References Cited

FOREIGN PATENT DOCUMENTS

| IN | 202411035583 | 5/2024 |
|---|---|---|
| WO | WO 02/062337 A1 | 8/2002 |
| WO | WO 2018/233663 A1 | 12/2018 |

OTHER PUBLICATIONS

M. S. T. Makki, et al., "Synthesis, voltammetric and analytical applications of some fluorine substituted spirosteroidalthiazolidin-4-one derivatives of sulla drugs", Journal of Chinese Chemical Society, vol. 63, Issue 2, Jan. 26, 2016, pp. 189-198 (10 pages).
Figueroa-Valverde. L. et al., "Syntheses and antibacterial activity of testosterone succinate-vitamin B-1 conjugate"; Asian Journal of Chemistry, 2010, pp. 3949-3958, abstract only (2 pages).

*Primary Examiner* — Brenda L Coleman
(74) *Attorney, Agent, or Firm* — Oblon, McClelland, Maier & Neustadt, L.L.P.

(57) ABSTRACT

A method for synthesizing testosterone-based thiazolidinone derivatives including preparing a testosterone thiosemicarbazone as an intermediate for building thiazolidinone structures through cyclization reactions. The synthesized testosterone-based thiazolidinone derivatives have antimicrobial activity against *Staphylococcus aureus* ATCC 6538-P (Gram-positive), *Escherichia coli* ATCC 25933, *Candida albicans* ATCC 10231, and *Aspergillus niger* NRRL-A326.

20 Claims, 11 Drawing Sheets

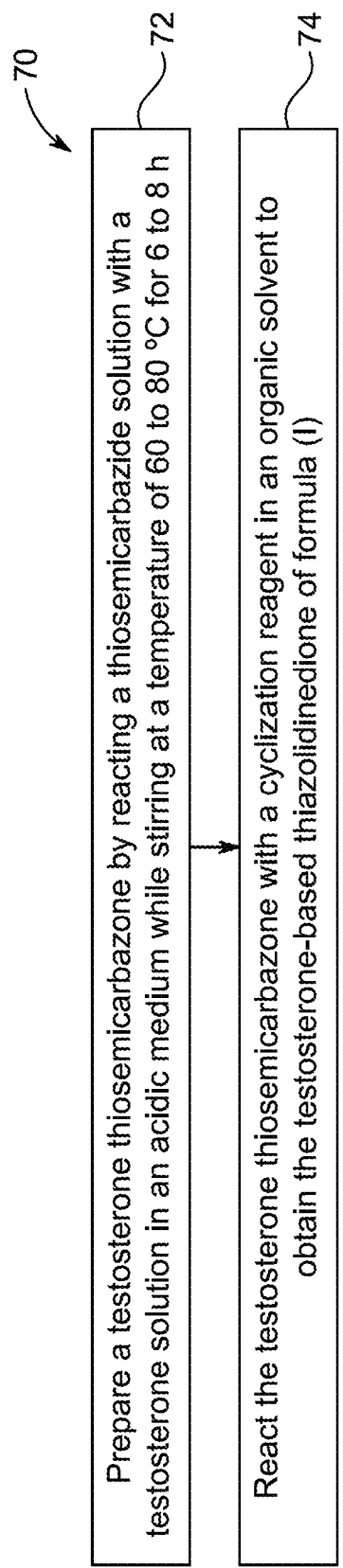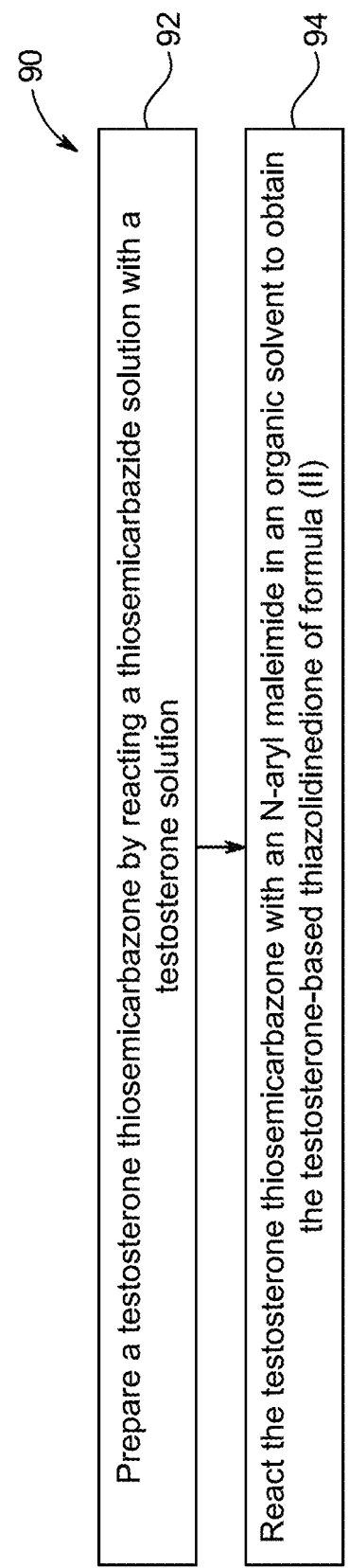
FIG. 1A
FIG. 1B

METHOD OF SYNTHESIZING TESTOSTERONE-BASED THIAZOLIDINONE DERIVATIVES

BACKGROUND

Technical Field

The present disclosure is directed to thiazolidinone derivatives, more particularly, to a method of synthesizing testosterone-based thiazolidinone derivatives and methods of its use in antimicrobial applications.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

The rise of antibiotic-resistant bacteria has become a serious global health concern. The World Health Organization (WHO) reported antimicrobial resistance as one of the top ten global public health threats facing humanity. Due to the expanding ineffectiveness of traditional antibiotics against multidrug-resistant pathogens, developing newer antimicrobial agents has become an urgent necessity.

Thiazolidinones have emerged as compounds of interest in medicinal chemistry due to their diverse biological activities, which encompass antimicrobial, anti-inflammatory, and anticancer properties. Thiazolidinones may inhibit vital enzymatic processes, cell wall synthesis, and the production of proteins in a wide array of microorganisms, potentially providing a substitute for conventional antibiotic therapies. Furthermore, the structural flexibility of thiazolidinones may play an important role in their antimicrobial efficacy. Thus, the biological activity of thiazolidinones may be tailored through chemical modifications to increase their antimicrobial efficacy, broaden their spectrum of activity, and decrease their toxicity, providing a suitable alternative to conventional therapies.

Accordingly, one objective of the present disclosure is to develop testosterone-based thiazolidinone derivatives that have the potential to circumvent established resistance pathways, thereby providing a new line of defense against resistant strains.

SUMMARY

In an exemplary embodiment, a method of synthesizing a testosterone-based thiazolidinone derivative is described. The method comprises preparing a testosterone thiosemicarbazone by reacting a thiosemicarbazide solution with a testosterone solution in an acidic medium while stirring at a temperature of 60 to 80° C. for 6 to 8 h, and reacting the testosterone thiosemicarbazone with a cyclization reagent in an organic solvent to obtain the testosterone-based thiazolidinone of Formula (I)

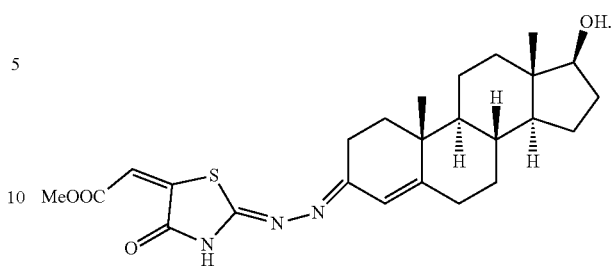

Formula (I)

The thiosemicarbazide solution comprises thiosemicarbazide dissolved in at least one selected from the group consisting of methanol, ethanol, isopropanol, propanol, acetone, ethylene glycol, glycerol, and tetrahydrofuran (THF).

In some embodiments, the thiosemicarbazide solution comprises thiosemicarbazide dissolved in at least one selected from the group consisting of methanol and ethanol.

In some embodiments, the acidic medium is at least one selected from the group consisting of acetic acid, citric acid, formic acid, oxalic acid, benzoic acid, carbonic acid, and phosphoric acid.

In some embodiments, the method of preparing the testosterone thiosemicarbazone comprises reacting the thiosemicarbazide solution with the testosterone solution in the acidic medium while stirring at a temperature of 65° C. for 7 h, and wherein the thiosemicarbazide solution comprises thiosemicarbazide dissolved in methanol In some embodiments, the method of preparing the testosterone thiosemicarbazone comprises reacting the thiosemicarbazide solution with the testosterone solution in the acidic medium while stirring at a temperature of 75° C. for 7 h, and wherein the thiosemicarbazide solution comprises thiosemicarbazide dissolved in ethanol.

In some embodiments, the acidic medium is acetic acid.

In some embodiments, the cyclization reagent is at least one selected from the group consisting of dimethyl acetylenedicarboxylate (DMAD), diethyl acetylenedicarboxylate (DEAD), di-tert-butyl acetylenedicarboxylate (DTBAD), and dibenzoyl acetylene (DBA).

In some embodiments, the method further comprises separating a testosterone thiosemicarbazone solution into a solid phase and a liquid phase; and drying the solid phase to obtain the testosterone thiosemicarbazone.

In some embodiments, the testosterone thiosemicarbazone solution has a molar ratio of testosterone to thiosemicarbazide of 1:5 to 5:1.

In some embodiments, the cyclization reagent is DMAD.

In some embodiments, the organic solvent is at least one selected from the group consisting of methanol, ethanol, isopropanol, propanol, acetone, ethylene glycol, glycerol, and THF.

In some embodiments, the organic solvent is acetone.

In an exemplary embodiment, a method of synthesizing a testosterone-based thiazolidinone derivative having antimicrobial activity is described. The method comprises preparing a testosterone thiosemicarbazone by reacting a thiosemicarbazide solution with a testosterone solution; and reacting the testosterone thiosemicarbazone with an N-aryl maleimide in an organic solvent to obtain the testosterone-based thiazolidinone of Formula (II)

Formula (II)

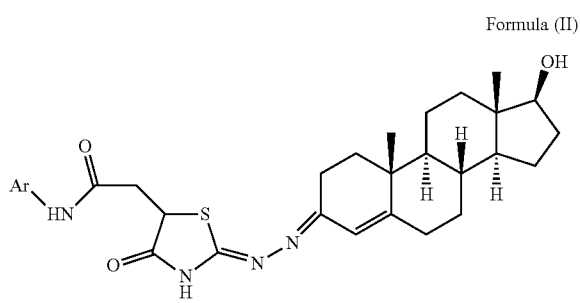

wherein Ar is C$_6$H$_5$, 4-ClC$_6$H$_4$, and C$_6$H$_4$—CH$_2$.

In some embodiments, the N-aryl maleimide is N-phenylmaleimide and Ar is C$_6$H$_5$.

In some embodiments, N-aryl maleimide is N-(4-chlorophenyl)maleimide and Ar is 4-ClC$_6$H$_4$.

In some embodiments, the N-aryl maleimide is N-benzylmaleimide and Ar is C$_6$H$_4$—CH$_2$.

In some embodiments, the organic solvent is acetone.

In some embodiments, the testosterone-based thiazolidinone derivative has an inhibition zone diameter of at least 25 mm against at least one of a *Staphylococcus aureus* gram-positive bacterium and an *Escherichia coli* gram-negative bacterium.

In some embodiments, the testosterone-based thiazolidinone derivative has an inhibition zone diameter of at least 15 mm against at least one of a *Staphylococcus aureus* gram-positive bacterium and an *Escherichia coli* gram-negative bacterium.

In some embodiments, the testosterone-based thiazolidinone derivative has an inhibition zone diameter of at least 20 mm against at least one of a *Candida albicans* fungus and an *Aspergillus niger* fungus.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 1A is a method flowchart for synthesizing a testosterone-based thiazolidinone derivative (compound (II)), according to certain embodiments.

FIG. 1B shows a method flowchart for synthesizing a testosterone-based thiazolidinone derivative having antimicrobial activity, according to certain embodiments.

DETAILED DESCRIPTION

Figure 2:
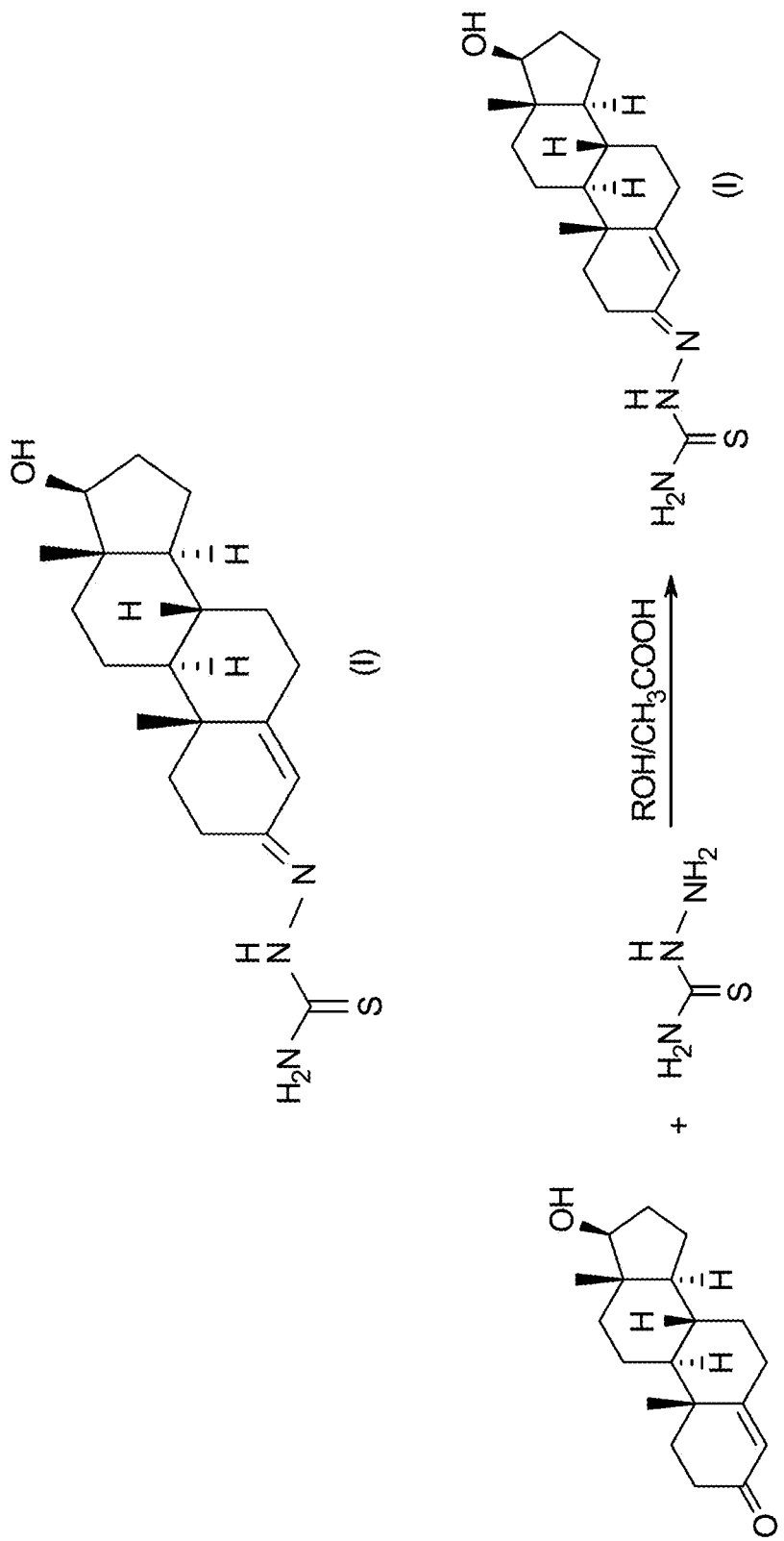
FIG. 2 illustrates a reaction scheme for preparing the testosterone thiosemicarbazone (compound (I)), according to certain embodiments.

When describing the present disclosure, the terms used are to be construed in accordance with the following definitions, unless a context dictates otherwise.

Embodiments of the present invention will now be described more fully hereinafter with reference to the accompanying drawings wherever applicable, in that some, but not all, embodiments of the disclosure are shown.

In the drawings, like reference numerals designate identical or corresponding parts throughout the several views. Further, as used herein, the words 'a,' 'an' and the like generally carry a meaning of 'one or more,' unless stated otherwise.

Furthermore, the terms 'approximately,' 'approximate,' 'about,' and similar terms generally refer to ranges that include the identified value within a margin of 20%, 10%, or preferably 5%, and any values therebetween.

As used herein, 'derivative' refers to a chemically or biologically modified version of a chemical compound that is structurally similar to a parent compound and derivable from that parent compound. A 'derivative' differs from an 'analogue' in that a parent compound may be the starting material to generate a 'derivative,' whereas the parent compound may not necessarily be used as the starting material to generate an 'analogue.' A derivative may or may not have different chemical or physical properties of the parent compound. For example, the derivative may be more hydrophilic, or it may have altered reactivity as compared to the parent compound. Derivatization (i.e., modification) may involve the substitution of one or more moieties within the molecule (e.g., a change in a functional group). The term 'derivative' also includes conjugates, and prodrugs of a parent compound (i.e., chemically modified derivatives that can be converted into the original compound under physiological conditions).

The terms 'compound' and 'derivative' as used herein, are used interchangeably, and refer to a chemical entity, whether in the solid, liquid, or gaseous phase, and whether in a crude mixture or purified and isolated.

The term 'compound' as used herein, refers to include the compounds disclosed in the present invention disclosure, salts, solvates, and mixtures, and known and unknown variations and forms thereof.

As used herein, the term 'solvate' refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

As used herein, "inhibition zone diameter" refers to a measurement that indicates how effective an antimicrobial is against a bacterium. The diameter of the zone of inhibition can be used to determine the level of sensitivity of the bacterium to the antimicrobial. In laboratory testing, such as the disk diffusion method (Kirby-Bauer test), a paper disk impregnated with the antimicrobial agent is placed on an agar plate inoculated with the microorganism. After incubation, the diameter of the clear zone (inhibition zone) around the disk is measured. The larger the inhibition zone, the more effective the antimicrobial agent is at preventing the growth of the microorganism.

As used herein, "antimicrobial activity" refers to the ability of a substance or agent to inhibit the growth of, or kill, microorganisms such as bacteria, fungi, viruses, or parasites. It may be measured by observing the substance's effectiveness in preventing the growth or replication of these microorganisms. The antimicrobial activity of a compound may be evaluated through laboratory tests, such as the disk diffusion method or minimum inhibitory concentration (MIC) determination.

The term 'aromatic compounds' or 'aromatic rings', as used herein, refers to hydrocarbon rings that, by the theory of Hickel, have a cyclic, delocalized (4n+2) pi-electron system. Non-limiting examples of aromatic compounds include benzene, benzene derivatives, compounds having at least one benzene ring in their chemical structure, toluene, ethylbenzene, p-xylene, m-xylene, mesitylene, durene, 2-phenylhexane, biphenyl, phenol, aniline, nitrobenzene, and the like.

The term 'aldehyde', as used herein, refers to an organic compound containing the group —CHO. The general formula of an aldehyde is the general formula for an aldehyde is $C_nH_{2n+1}$— CHO, where n represents the number of atoms. Non-limiting examples of aldehydes include formaldehyde, acetaldehyde, propionaldehyde, butyraldehyde, isovaleraldehyde, and benzaldehyde.

The term 'ketone', as used herein, refers to an organic compound having a carbonyl group (C=O) with the carbon atom bonded to two other carbon groups. The general formula of a ketone is $C_nH_{2n}O$, where n represents the number of atoms. Non-limiting examples of ketones include acetone, butanone, cyclohexanone, and oxaloacetate.

The term 'thiosemicarbazide', as used herein, refers to an organic compound with the chemical formula $H_2N$—NH—CS—$NH_2$. Thiosemicarbazides are derivatives of semicarbazide, where the oxygen atom in the carbonyl group (C=O) is replaced by a sulfur atom, forming a thioketo group (C=S). Thiosemicarbazides may used as a building block in organic synthesis and can react with various aldehydes, ketones, and other compounds to form thiosemicarbazones.

The term 'thiosemicarbazones', as used herein, refers to an organosulfur compound with the chemical formula $H_2NCSNHN=CR_2$. Thiosemicarbazones may be used as chelators due to their ability to bind to a variety of metal ions, including copper, iron, zinc, cobalt, rhenium, gallium, and indium. Thiosemicarbazones may be prepared by condensing a ketone or aldehyde with a thiosemicarbazide.

The term 'thiazolidinone', as used herein, refers to a class of heterocyclic organic compounds with the formula $(CH_2)_2CO(NH)S$. Thiazolidinones are a 5-membered saturated ring with a thioether group and an amine group in the 1 and 3 positions.

The term 'cyclization reagent', as used herein, refers to chemical compounds used to induce the formation of cyclic structures in organic molecules by facilitating an intramolecular reaction, often involving catalysts like metal complexes, strong acids, or radical initiators, depending on the desired ring size and functional groups present in the starting material. Some common examples include organotin hydrides, iodine, Lewis acids (e.g., aluminum chloride), samarium diiodide, oxaziridines, and various transition metal catalysts which can initiate radical or concerted cyclization pathways depending on the reaction conditions Aspects of the present disclosure are directed toward a synthetic method for synthesizing testosterone-based thiazolidinone derivatives. The process utilizes testosterone thiosemicarbazone as an intermediate, which undergoes cyclization reactions to form thiazolidinone structures. The antimicrobial properties of the testosterone-based thiazolidinone derivatives are evaluated against *Staphylococcus aureus, Escherichia coli, Candida albicans*, and *Aspergillus niger*.

FIG. 1A illustrates a flow chart of a method 70 of synthesizing a testosterone-based thiazolidinone derivative. The order in which the method 70 is described is not intended to be construed as a limitation, and any number of the described method steps can be combined in any order to implement the method 70. Additionally, individual steps may be removed or skipped from the method 70 without departing from the spirit and scope of the present disclosure.

At step 72, the method 70 comprises preparing a testosterone thiosemicarbazone by reacting a thiosemicarbazide solution with a testosterone solution in an acidic medium while stirring at a temperature of 60 to 80° C. for 6 to 8 h. In some embodiments, the reacting comprises reacting a thiosemicarbazide solution with a testosterone solution in an acidic medium while stirring at a temperature of 61 to 79° C., preferably 62 to 78° C., preferably 63 to 77° C., preferably 64 to 76° C., most preferably 65 to 75° C. In another embodiment, the reacting comprises reacting a thiosemicarbazide solution with a testosterone solution in an acidic medium while stirring for 5 to 10 h, preferably 5.5 to 9.5 h, preferably 6 to 9 h, preferably 6.5 to 8.5 h, preferably 7 to 8 h, preferably 7 to 7.5 h, most preferably 7 hours. In another embodiment, the reacting comprises reacting the thiosemicarbazide solution with the testosterone solution in an acidic medium in a molar ratio of 1:5 to 5:1 of thiosemicarbazide to testosterone. In some embodiments, the molar ratio is 1:4 to 4:1 thiosemicarbazide to testosterone, preferably 1:3 to 3:1, preferably 1:2 to 2:1, most preferably 1:1 thiosemicarbazide to testosterone.

In an embodiment, the thiosemicarbazide solution comprises thiosemicarbazide dissolved in at least one solvent selected from the group consisting of methanol, ethanol, isopropanol, propanol, acetone, ethylene glycol, glycerol, and tetrahydrofuran (THF). In a preferred embodiment, the thiosemicarbazide solution comprises thiosemicarbazide dissolved in at least one solvent selected from the group consisting of methanol and ethanol. The choice of solvent may affect the temperature utilized during the reacting because different solvents have varying abilities to absorb or release heat during a chemical reaction. In some embodiments, when the thiosemicarbazide solution comprises thiosemicarbazide dissolved in methanol, the testosterone thiosemicarbazone is preferably prepared by reacting the thiosemicarbazide solution with the testosterone solution in the acidic medium while stirring at a temperature of 60 to 65° C., preferably 60.5 to 65° C., preferably 61 to 65° C., preferably 61.5 to 65° C., preferably 62 to 65° C., preferably 62.5 to 65° C., preferably 63 to 65° C., preferably 63.5 to 65° C., preferably 64 to 65° C., preferably 64.5 to 65° C., most preferably 65° C. In another embodiment, when the thiosemicarbazide solution comprises thiosemicarbazide dissolved in ethanol, the testosterone thiosemicarbazone is preferably prepared by reacting the thiosemicarbazide solution with the testosterone solution in the acidic medium while stirring at a temperature of 70 to 75° C., preferably 70.5 to 75° C., preferably 71 to 75° C., preferably 71.5 to 75° C., preferably 72 to 75° C., preferably 72.5 to 75° C., preferably 73 to 75° C., preferably 73.5 to 75° C., preferably 74 to 75° C., preferably 74.5 to 75° C., most preferably 75° C.

In some embodiments, the acidic medium is at least one selected from the group consisting of acetic acid, citric acid, formic acid, lactic acid, oxalic acid, benzoic acid, carbonic acid, and phosphoric acid. In some embodiments, the acidic medium may include hydrochloric acid, sulfuric acid, tartaric acid, lactic acid, malic acid, and propionic acid. An acidic medium may be used in cyclization reactions because the presence of protons (H⁺) can activate the necessary nucleophilic sites on the molecule by protonating them, making them more susceptible to attack and facilitating the ring-closing step. In another embodiment, the acidic medium is preferably a weak acid. A weak acid is an acid that only partially ionizes when dissolved in water, meaning it does not fully dissociate into its constituent ions, resulting in a relatively low concentration of hydrogen ions in solution. Suitable weak acids include, but are not limited to, acetic acid, citric acid, and lactic acid. In some embodiments, the acidic medium is at least one selected from the group consisting of acetic acid, citric acid, and lactic acid. In a preferred embodiment, the acidic medium is acetic acid. After the reaction between testosterone and thiosemicarbazide in the acidic medium, the testosterone thiosemicarbazone may precipitate out due to its lower solubility in the reaction medium. Therefore, the method comprises separating a testosterone thiosemicarbazone solution into a solid phase and a liquid phase. The separation of the testosterone thiosemicarbazone solution into a solid phase and a liquid phase may be performed by any suitable method known to one of ordinary skill in the art including, but not limited to, filtration, centrifugation, or decantation after a reaction or crystallization. The solid phase comprises a precipitated material comprising the testosterone thiosemicarbazone, while the liquid phase comprises other dissolved substances. After separation, the method further comprises drying the solid phase to obtain the testosterone thiosemicarbazone. The method of drying is not particularly limited and may be any method of drying in the art. In some embodiments, the drying may be performed by using heating appliances such as ovens, microwaves, autoclaves, hot plates, heating mantles and tapes.

At step 74, the method 70 comprises reacting the testosterone thiosemicarbazone with a cyclization reagent in an organic solvent to obtain the testosterone-based thiazolidinone of Formula (I)

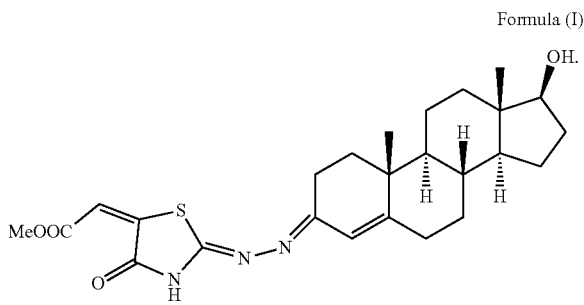

Formula (I)

The cyclization reagent may facilitate the formation of a cyclic compound from a linear molecule by introducing a reactive site that allows for an intramolecular bond formation between two functional groups within the molecule, essentially "closing the ring" to create a cyclic structure. In one embodiment, the cyclization reagent is at least one selected from the group consisting of dimethyl acetylenedicarboxylate (DMAD), diethyl acetylenedicarboxylate (DEAD), di-tert-butyl acetylenedicarboxylate (DTBAD), and dibenzoyl acetylene (DBA). In a preferred embodiment, the cyclization reagent is DMAD.

In some embodiments, the reacting comprises reacting the testosterone thiosemicarbazone with the cyclization reagent in a molar ratio of the testosterone thiosemicarbazone to cyclization agent of 1:5 to 5:1. In another embodiment, the molar ratio of testosterone thiosemicarbazone to the cyclization reagent is 1:4 to 4:1, preferably 1:3 to 3:1, preferably 1:2 to 2:1, most preferably 1:1 testosterone thiosemicarbazone to cyclization reagent.

In some embodiments, the reacting comprises reacting the testosterone thiosemicarbazone with a cyclization reagent in an organic solvent. Suitable organic solvents may include, but are not limited to, ethanol, isopropanol, acetone, ethylene glycol, glycerol, THF, n-butanol, methanol, or any combination thereof. In a preferred embodiment, the organic solvent is acetone.

FIG. 1B illustrates a flow chart of a method 90 of synthesizing a testosterone-based thiazolidinone derivative having antimicrobial activity. The order in which the method 90 is described is not intended to be construed as a limitation, and any number of the described method steps can be combined in any order to implement the method 90. Additionally, individual steps may be removed or skipped from the method 90 without departing from the spirit and scope of the present disclosure.

At step 92, the method 90 comprises preparing a testosterone thiosemicarbazone by reacting a thiosemicarbazide solution with a testosterone solution. In some embodiments, the reacting comprises reacting a thiosemicarbazide solution with a testosterone solution in an acidic medium while stirring at a temperature of 61 to 79° C., preferably 62 to 78° C., preferably 63 to 77° C., preferably 64 to 76° C., most preferably 65 to 75° C. In another embodiment, the reacting comprises reacting a thiosemicarbazide solution with a testosterone solution in an acidic medium while stirring for 5 to 10 h, preferably 5.5 to 9.5 h, preferably 6 to 9 h, preferably 6.5 to 8.5 h, preferably 7 to 8 h, preferably 7 to 7.5 h, most preferably 7 hours. In another embodiment, the reacting comprises reacting the thiosemicarbazide solution with the testosterone solution in an acidic medium in a molar ratio of 1:5 to 5:1 of thiosemicarbazide to testosterone. In some embodiments, the molar ratio is 1:4 to 4:1 thiosemicarbazide to testosterone, preferably 1:3 to 3:1, preferably 1:2 to 2; 1, most preferably 1:1 thiosemicarbazide to testosterone.

In an embodiment, the thiosemicarbazide solution comprises thiosemicarbazide dissolved in at least one solvent selected from the group consisting of methanol, ethanol, isopropanol, propanol, acetone, ethylene glycol, glycerol, and tetrahydrofuran (THF). In a preferred embodiment, the thiosemicarbazide solution comprises thiosemicarbazide dissolved in at least one solvent selected from the group consisting of methanol and ethanol. The choice of solvent may affect the temperature utilized during the reacting because different solvents have varying abilities to absorb or release heat during a chemical reaction. In some embodiments, when the thiosemicarbazide solution comprises thiosemicarbazide dissolved in methanol, the testosterone thiosemicarbazone is preferably prepared by reacting the thiosemicarbazide solution with the testosterone solution in the acidic medium while stirring at a temperature of 60 to 65° C., preferably 60.5 to 65° C., preferably 61 to 65° C., preferably 61.5 to 65° C., preferably 62 to 65° C., preferably 62.5 to 65° C., preferably 63 to 65° C., preferably 63.5 to 65° C., preferably 64 to 65° C., preferably 64.5 to 65° C., most preferably 65° C. In another embodiment, when the thiosemicarbazide solution comprises thiosemicarbazide dissolved in ethanol, the testosterone thiosemicarbazone is preferably prepared by reacting the thiosemicarbazide solution with the testosterone solution in the acidic medium while stirring at a temperature of 70 to 75° C., preferably 70.5 to 75° C., preferably 71 to 75° C., preferably 71.5 to 75° C., preferably 72 to 75° C., preferably 72.5 to 75° C., preferably 73 to 75° C., preferably 73.5 to 75° C., preferably 74 to 75° C., preferably 74.5 to 75° C., most preferably 75° C.

In some embodiments, the acidic medium is at least one selected from the group consisting of acetic acid, citric acid, formic acid, lactic acid, oxalic acid, benzoic acid, carbonic acid, and phosphoric acid. In some embodiments, the acidic medium may include hydrochloric acid, sulfuric acid, tartaric acid, lactic acid, malic acid, and propionic acid. An acidic medium may be used in cyclization reactions because the presence of protons (H+) can activate the necessary nucleophilic sites on the molecule by protonating them, making them more susceptible to attack and facilitating the ring-closing step. In another embodiment, the acidic medium is preferably a weak acid. A weak acid is an acid that only partially ionizes when dissolved in water, meaning it does not fully dissociate into its constituent ions, resulting in a relatively low concentration of hydrogen ions in solution. Suitable weak acids include, but are not limited to, acetic acid, citric acid, and lactic acid. In some embodiments, the acidic medium is at least one selected from the group consisting of acetic acid, citric acid, and lactic acid. In a preferred embodiment, the acidic medium is acetic acid.

After the reaction between testosterone and thiosemicarbazide in the acidic medium, the testosterone thiosemicarbazone may precipitate out due to its lower solubility in the reaction medium. Therefore, the method comprises separating a testosterone thiosemicarbazone solution into a solid phase and a liquid phase. The separation of the testosterone thiosemicarbazone solution into a solid phase and a liquid phase may be performed by any suitable method known to one of ordinary skill in the art including, but not limited to, filtration, centrifugation, or decantation after a reaction or crystallization. The solid phase comprises a precipitated material comprising the testosterone thiosemicarbazone, while the liquid phase comprises other dissolved substances. After separation, the method further comprises drying the solid phase to obtain the testosterone thiosemicarbazone. The method of drying is not particularly limited and may be any method of drying in the art. In some embodiments, the drying may be performed by using heating appliances such as ovens, microwaves, autoclaves, hot plates, heating mantles and tapes.

At step 94, the method 90 comprises reacting the testosterone thiosemicarbazone with an N-aryl maleimide in an organic solvent to obtain the testosterone-based thiazolidinone of Formula (II)

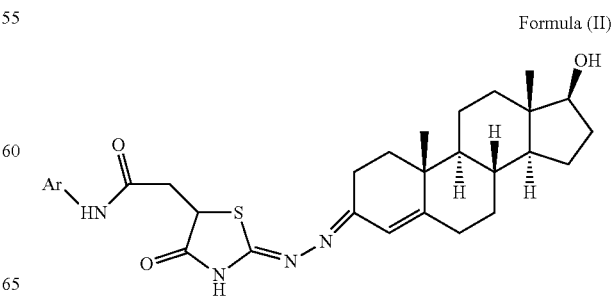

Formula (II)

where Ar is at least one selected from the group consisting of $C_6H_5$, 4-$ClC_6H_4$, and $C_6H_4$—$CH_2$.

N-aryl maleimides may be used in cyclization reactions to create cyclic structures containing a sulfur atom, as N-aryl maleimides readily react with thiol groups through a Michael addition, forming a stable thiosuccinimide linkage to close the ring structure. N-aryl maleimides have increased selectivity for thiol groups, allowing for precise cyclization reactions even in the presence of other nucleophiles. In an embodiment, the N-aryl maleimide is at least one of N-phenylmaleimide, N-(4-chlorophenyl)maleimide, and N-benzylmaleimide. In a specific embodiment, the N-aryl maleimide is N-phenylmalemide and the Ar of Formula (II) is $C_6H$. In another specific embodiment, the N-aryl maleimide is N-(4-chlorophenyl)maleimide the Ar of Formula (II) is 4-$ClC_6H_4$. In yet another specific embodiment, the N-aryl maleimide is N-benzylmaleimide and the Ar of Formula (II) is $C_6H_4$—$CH_2$. In some embodiments, the reacting comprises reacting the testosterone thiosemicarbazone with the N-aryl maleimide in an organic solvent. Suitable organic solvents may include, but are not limited to, methanol, ethanol, isopropanol, acetone, ethylene glycol, glycerol, or any combination thereof. In a preferred embodiment, the organic solvent is acetone.

In some embodiments, the reacting comprises reacting the testosterone thiosemicarbazone with the N-aryl maleimide in a molar ratio of the testosterone thiosemicarbazone to N-aryl maleimide of 1:5 to 5:1. In another embodiment, the molar ratio of testosterone thiosemicarbazone to the N-aryl maleimide is 1:4 to 4:1, preferably 1:3 to 3:1, preferably 1:2 to 2:1, most preferably 1:1 testosterone thiosemicarbazone to N-aryl maleimide.

In some embodiments, the testosterone-based thiazolidinone derivative (compound II) has antimicrobial activity against at least one selected from the group consisting of a gram-positive bacterium, a gram-negative bacterium, and a fungus. In some embodiments, the gram-positive bacterium is at least one selected form the group consisting of a *Staphylococcus aureus, Streptococcus pneumoniae, Streptococcus pyogenes, Enterococcus faecalis, Bacillus anthracis, Clostridium tetani, Clostridium botulinum, Corynebacterium diphtheriae, Listeria monocytogenes*, and *Staphylococcus epidermidis*. In a preferred embodiment, the gram-positive bacterium is *Staphylococcus aureus*. In some embodiments, the gram-negative bacterium is at least one selected from the group consisting of *Klebsiella pneumoniae, Pseudomonas aeruginosa, Acinetobacter baumannii, Escherichia coli, Haemophilus influenzae, Citrobacter koseri*, and *Salmonella typhi*. In a preferred embodiment, the gram-negative bacterium is *Escherichia coli*. In some embodiments, the fungus is at least one selected form the group consisting of *Candida albicans, Candida glabrata, Aspergillus fumigatus, Cryptococcus neoformans, Aspergillus niger, Candida krusei*, and *Aspergillus flavus*. In a preferred embodiment, the fungus is at least one selected from the group of *Aspergillus niger* and *Candida albicans*.

In an embodiment, the testosterone-based thiazolidinone (compound II) has an inhibition zone diameter of at least 29 mm against *Staphylococcus aureus* gram-positive bacterium. In another embodiment, the testosterone-based thiazolidinone (compound II) has an inhibition zone diameter of at least 26 mm against *Escherichia coli* gram-negative bacterium. In an embodiment, the testosterone-based thiazolidinone (compound II) has an inhibition zone diameter of at least 29 mm against *Candida albicans*.

In one embodiment, the testosterone-based thiazolidinone derivative of Formula (II) (compound III) where Ar is $C_6H_5$ has an inhibition zone diameter of at least 35 mm against *Staphylococcus aureus* gram-positive bacterium. In another embodiment, the testosterone-based thiazolidinone derivative of Formula (II) where Ar is $C_6H_5$ has an inhibition zone diameter of at least 32 mm against *Escherichia coli* gram-negative bacterium. In an embodiment, the testosterone-based thiazolidinone derivative of Formula (II) where Ar is $C_6H_5$ has an inhibition zone diameter of at least 36 mm against *Candida albicans*. In another embodiment, the testosterone-based thiazolidinone derivative of Formula (II) where Ar is $C_6H_5$ has an inhibition zone diameter of at least 37 mm against *Aspergillus niger*.

In one embodiment, the testosterone-based thiazolidinone derivative of Formula (II) (compound III) where Ar is 4-$ClC_6H_4$ has an inhibition zone diameter of at least 38 mm against *Staphylococcus aureus* gram-positive bacterium. In another embodiment, the testosterone-based thiazolidinone derivative of Formula (II) where Ar is 4-$ClC_6H_4$ has an inhibition zone diameter at least 39 mm against *Escherichia coli* gram-negative bacterium. In an embodiment, the testosterone-based thiazolidinone derivative of Formula (II) where Ar is 4-$ClC_6H_4$ has an inhibition zone diameter of at least 41 mm against *Candida albicans*. In another embodiment, the testosterone-based thiazolidinone derivative of Formula (II) where Ar is 4-$ClC_6H_4$ has an inhibition zone diameter of at least 43 mm against *Aspergillus niger*.

In one embodiment, the testosterone-based thiazolidinone derivative of Formula (II) (compound III) where Ar is $CH_2C_6H_4$ has an inhibition zone diameter of at least at least 19 mm against *Staphylococcus aureus* gram-positive bacterium. In another embodiment, the testosterone-based thiazolidinone derivative of Formula (II) where Ar is $CH_2C_6H_4$ has an inhibition zone diameter at least 17 mm against *Escherichia coli* gram-negative bacterium. In an embodiment, the testosterone-based thiazolidinone derivative of Formula (II) where Ar is $CH_2C_6H_4$ has an inhibition zone diameter of at least 21 mm against *Candida albicans*. In another embodiment, the testosterone-based thiazolidinone derivative of Formula (II) where Ar is $CH_2C_6H_4$ has an inhibition zone diameter of at least 44 mm against *Aspergillus niger*.

EXAMPLES

The following examples demonstrate a method for synthesizing testosterone-based thiazolidinone derivatives. The examples are provided solely for illustration and are not to be construed as limitations of the present disclosure, as many variations thereof are possible without departing from the spirit and scope of the present disclosure.

Example 1: General Methodology Adopted to Synthesize and Evaluate the Antimicrobial Activity of Testosterone-Based Thiazolidinone Derivatives The reaction conditions and mechanisms are described in subsequent examples. The successful fabrication of the testosterone-based thiazolidinone derivatives was confirmed by different analytical techniques. The antimicrobial activity of newly prepared testosterone-based thiazolidinone derivatives was evaluated against various microorganisms, including *Staphylococcus aureus* ATCC 6538-P, *Escherichia coli* ATCC 25933, *Candida albicans* ATCC 10231, and *Aspergillus niger* NRRL-A326. The synthesized testosterone-based thiazolidinone derivatives demonstrated promising antimicrobial properties.

Example 2: Preparation of 17-hydroxy-10,13-dimethyl 1,2,6,7,8,9,10,11,12,13,14, 15,16,17-tetradecahydro-3H-cyclopentaphenanthren-3-ylidene)hydrazine-1-carbothioamide (compound I)

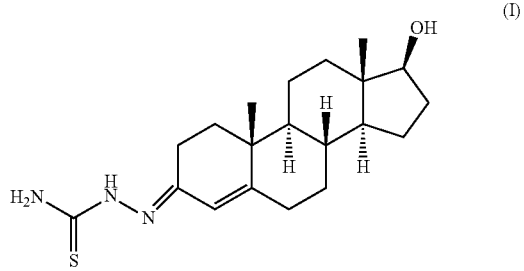

Figure 3:
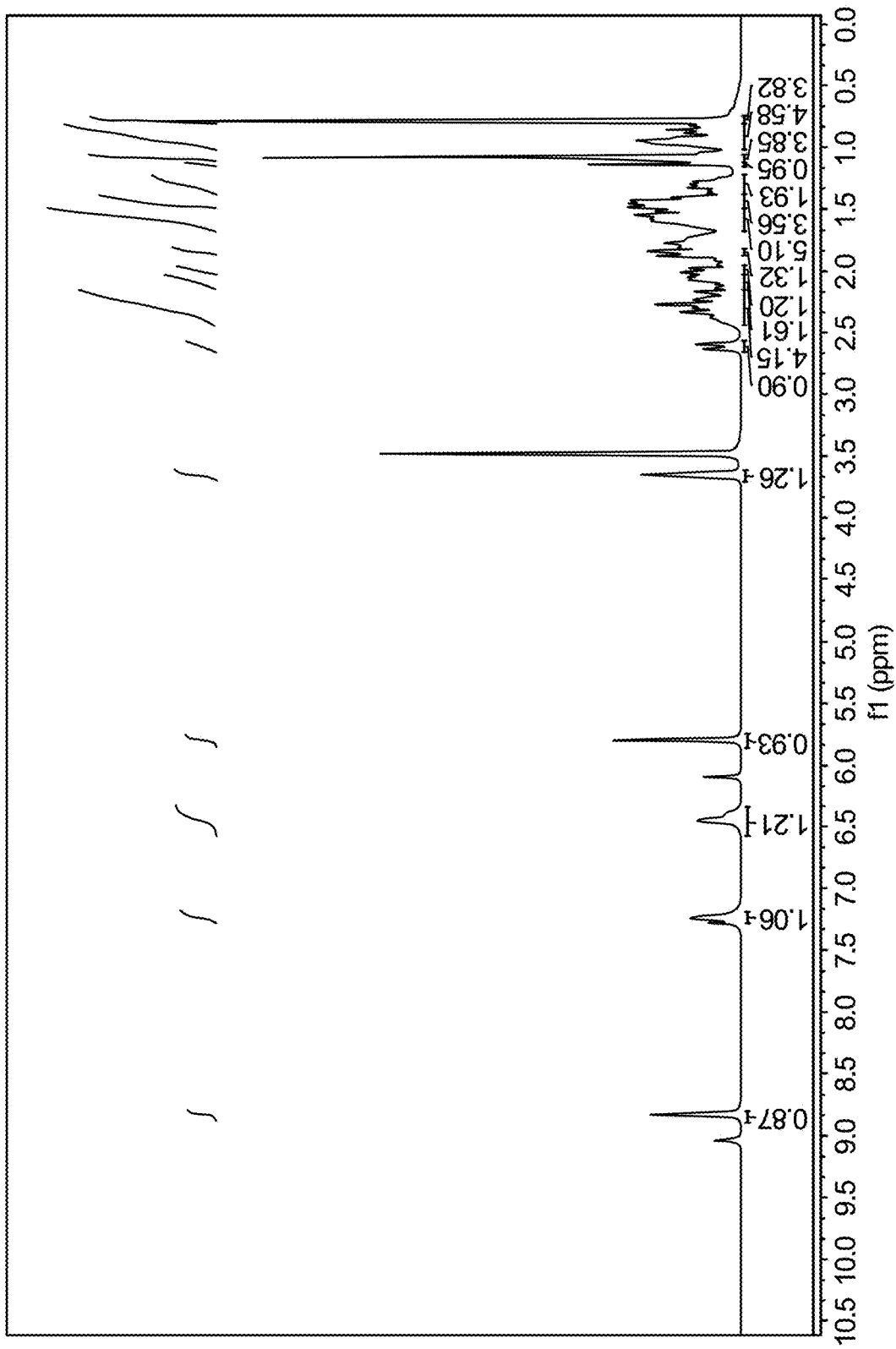
FIG. 3 shows a proton-nuclear magnetic resonance spectroscopy ($^1$H-NMR) spectrum of compound (I) in CDCl$_3$, according to certain embodiments.

The compound (I) was prepared by mixing a mixture of testosterone (0.288 g, 1 mmol) and thiosemicarbazide (0.091 g, 1 mmol) in 25 mL methanol or ethanol in the presence of a catalytic amount of acetic acid and heating under reflux at 65 or 75° C. while stirring. The mixtures were stirred at 65° C. when MeOH was used and at 75° C. when EtOH was used. The mixing was carried out for about 7 h (monitored by TLC). After cooling, the solids formed were filtered off, dried, and recrystallized from ethanol as white crystals. (yield 93%). The reaction scheme for synthesizing compound (I) is presented in FIG. 2. IR (KBr) v/cm$^{-1}$: 3416 (NH$_2$), 2955 (CH$_{alkyl}$), 1585 (C=N). $^1$H-NMR (400 MHz) CDCl$_3$, δ (ppm): 0.72 (3H, s, CH$_3$), 0.82-0.86 (1H, m, CH), 0.98 (2H, t, CH$_2$), 1.08 (3H, s, CH$_3$), 1.13 (1H, m, CH), 1.29 (1H, m, CH), 1.35-1.45 (2H, m, CH$_2$), 1.48-1.55 (2H, m, CH$_2$), 1.59 (2H, m, CH$_2$), 1.60-1.65 (2H, m, CH$_2$), 1.98-2.09 (2H, m, CH$_2$), 2.20-2.28 (2H, m, CH$_2$), 2.33-2.63 (2H, m, CH$_2$), 3.67 (1H, t, CH), 5.8 (1H, s, CH=), 6.45-7.23 (2H, d,d, NH$_2$), 8.82 (1H, s, NH) (FIG. 3).

Example 3: Preparation of methyl-17-hydroxy-10,13-dimethyl-1,2,6,7,8,9,10,11,12,13,14,15,16,17-tetradecahydro-3H-cyclopentaphenanthren-3-ylidene)hydrazono)-4-oxothiazolidin-5-ylidene)acetate (compound II)

Figure 4:
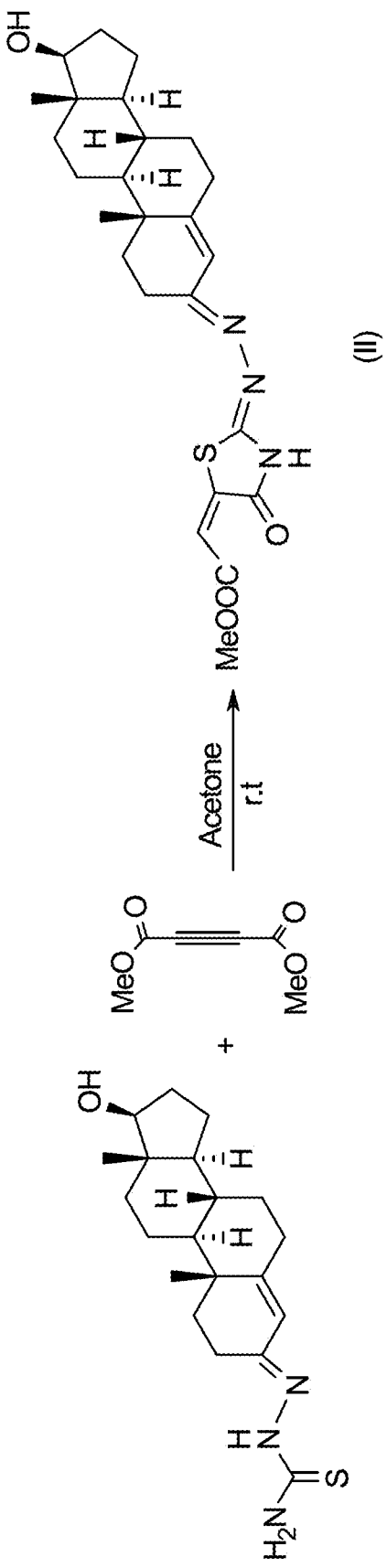
FIG. 4 illustrates a reaction scheme for the compound (II) by treatment with dimethyl acetylenedicarboxylate (DMAD), according to certain embodiments.
Figure 5:
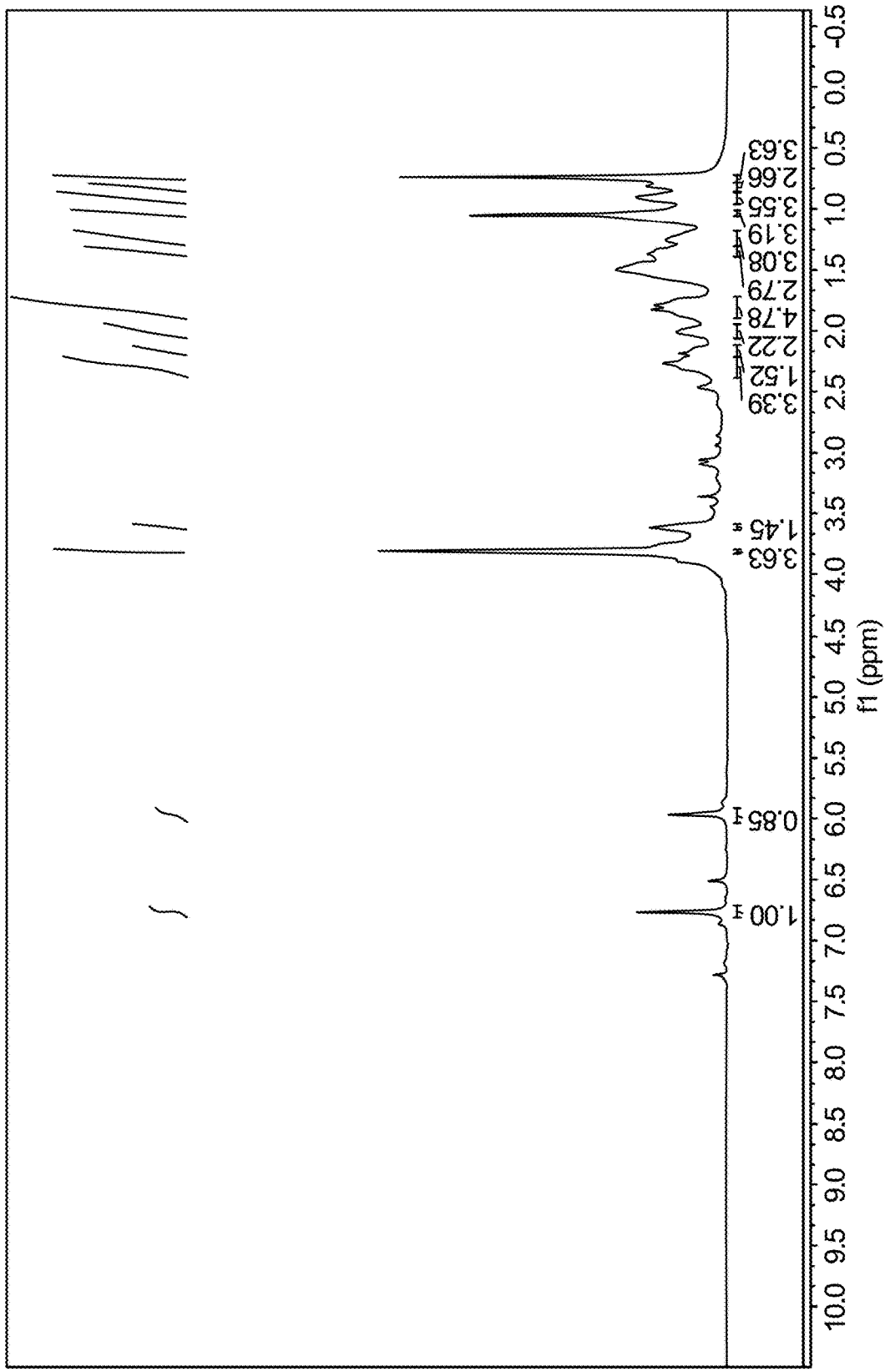
FIG. 5 shows $^1$H-NMR spectrum of compound (II) in CDCl$_3$, according to certain embodiments.
Figure 6:
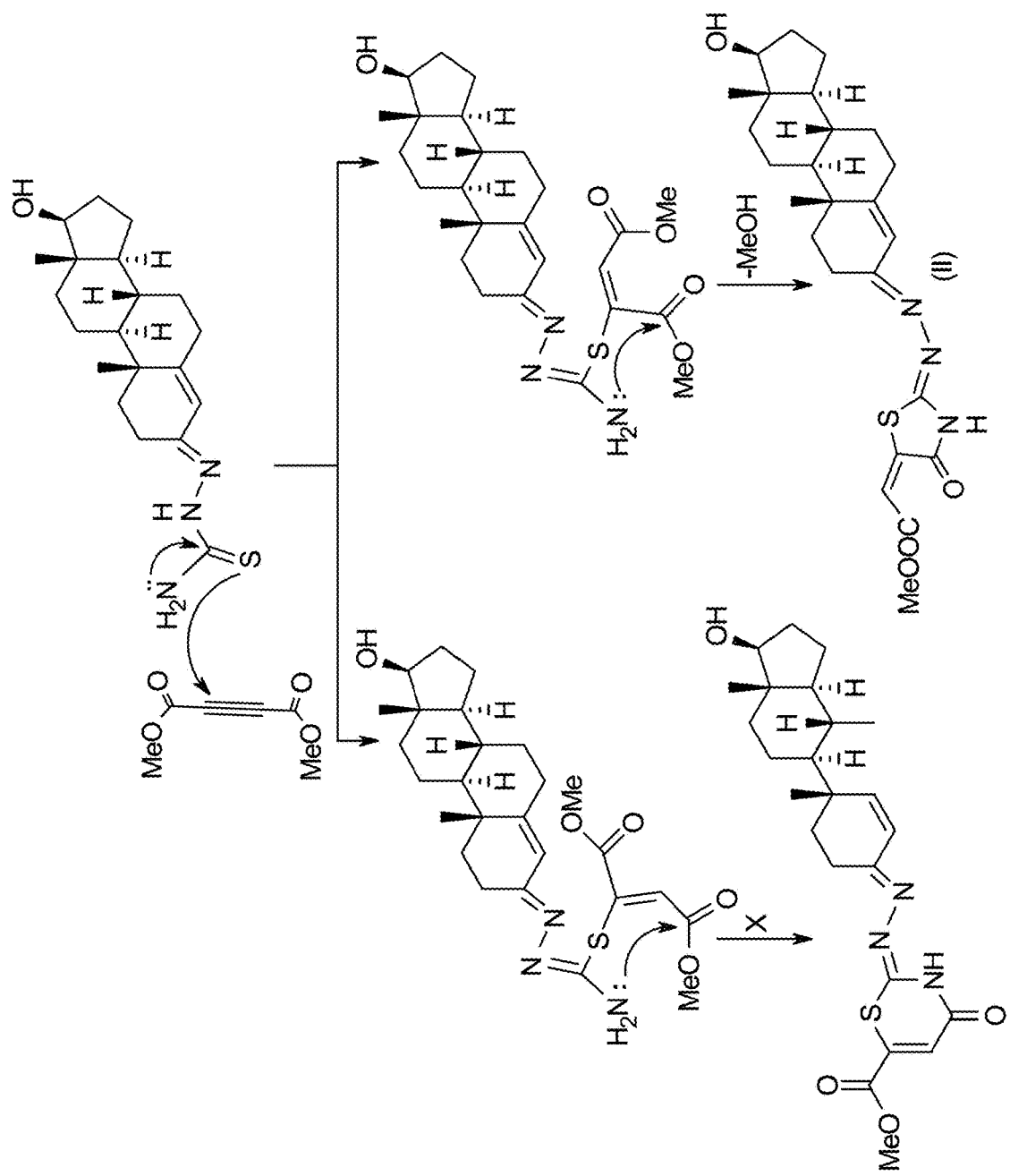
FIG. 6 shows a proposed reaction mechanism for obtaining the compound (II), according to certain embodiments.

Dimethyl acetylene dicarboxylate (DMAD) (0.038 g, 0.035 mL, 0.27 mmol) was added dropwise to a solution of compound (I) (0.1 g, 0.27 mmol) in acetone (20 mL) while stirring. Upon the addition of DMAD, the color of the solution turned yellow. The stirring was continued at room temperature (25° C.) until TLC indicated completed consumption of the compound (I) (7 h.), then the solution was allowed to cool overnight. The formed precipitate was filtered and recrystallized from methanol as yellow crystals (yield 87%). The reaction scheme for synthesizing compound (II) is presented in FIG. 4. IR (KBr) v/cm$^{-1}$: 3447 (OH), 2943 (CH$_{alkyl}$), 1712 (C=O), 1623 (C=N). $^1$H-NMR (400 MHz) DMSO-d$_6$, δ (ppm): 0.69 (3H, s, CH$_3$), 0.80 (1H, m, CH), 0.83 (1H, m, CH), 0.87 (1H, m, CH), 0.89 (2H, t, CH$_2$), 1.05 (3H, s, CH$_3$), 1.23 (2H, m, CH$_2$), 1.33-1.37 (2H, m, CH$_2$), 1.74-1.77 (2H, m, CH$_2$), 1.83-1.87 (2H, m, CH$_2$), 2.01 (2H, m, CH$_2$), 2.14-2.23 (2H, m, CH$_2$), 2.27-2.35 (2H, m, CH$_2$), 3.61 (1H, t, CH), 3.80 (3H, m, CH$_3$), 5.96 (1H, s, CH=), 6.76 (1H,s, —S—CH=) (FIG. 5).

Example 4: Preparation of 17-hydroxy-10,13-dimethyl-1,2,6,7,8,9,10,11,12,13,14,15,16,17-tetradecahydro-3H-cyclopentaphenanthren-3-ylidene)hydrazono)-4-oxothiazolidin-5-yl)-N-arylacetamide derivatives of Formula ((II))

Figure 7:
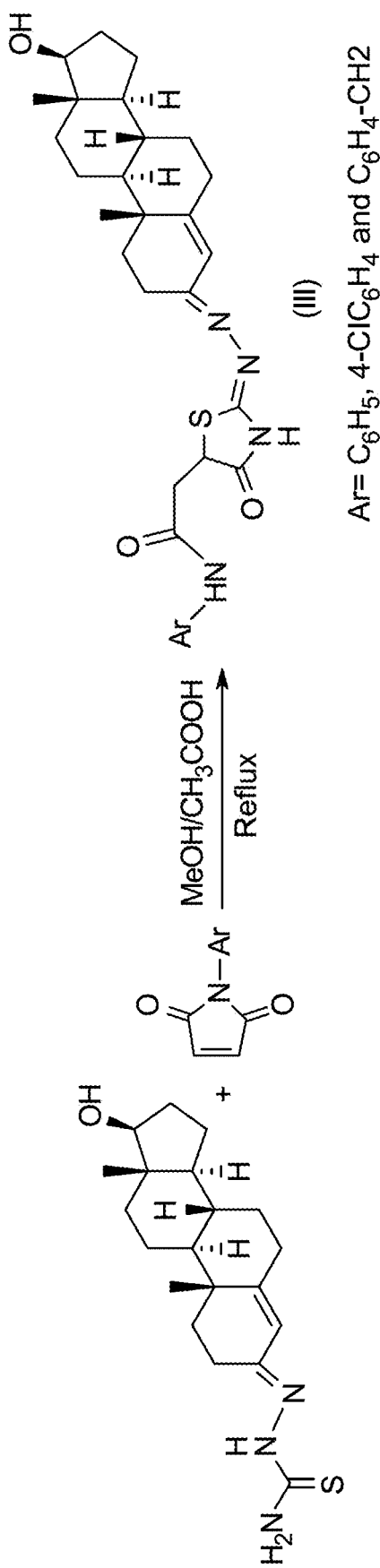
FIG. 7 illustrates a reaction scheme for preparing a compound of Formula (II) (compound III) by treatment with N-aryl maleimides, according to certain embodiments.
Figure 8:
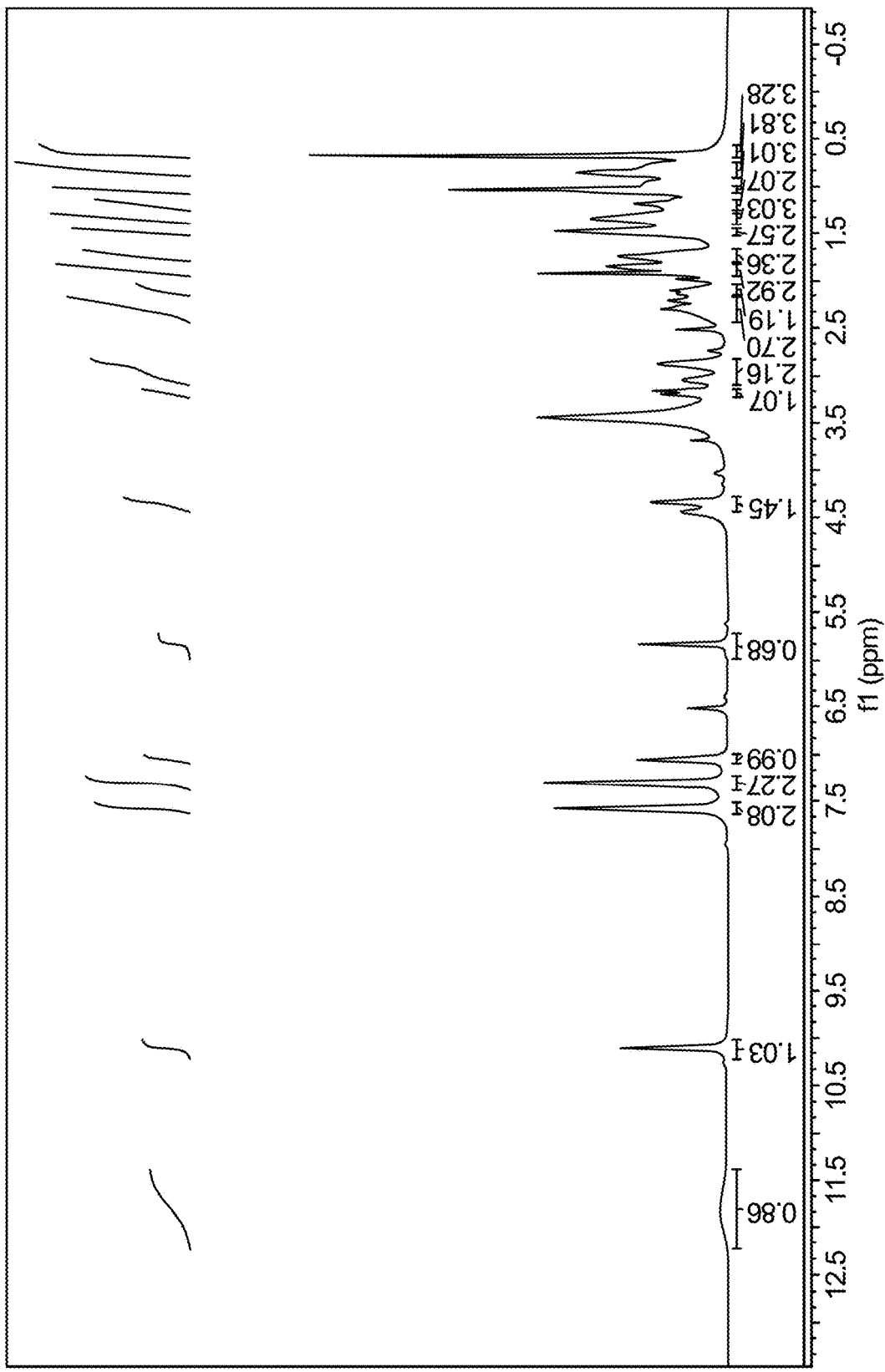
FIG. 8 shows $^1$H-NMR spectrum of a compound (III) (Ar is C$_6$H$_5$) in DMSO-d$_6$, according to certain embodiments.
Figure 9:
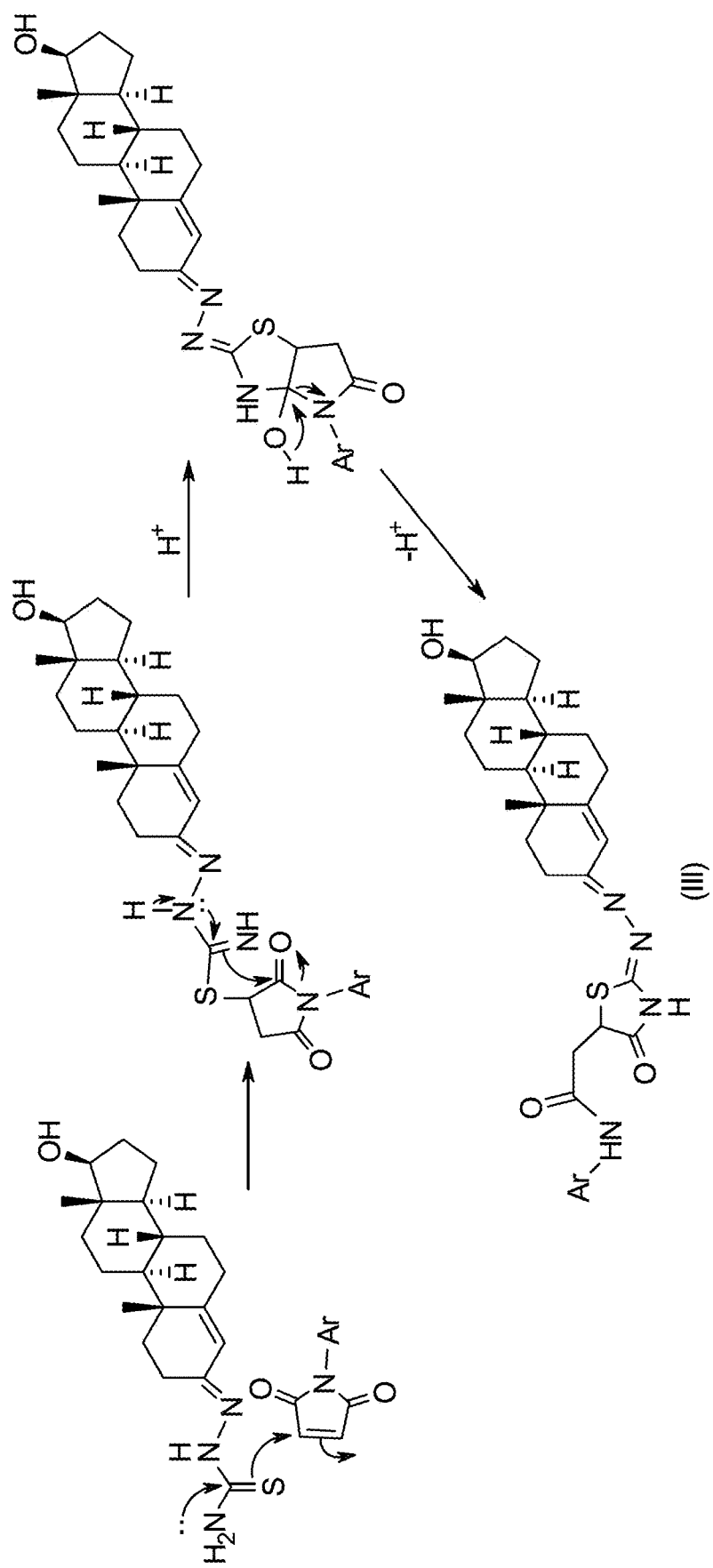
FIG. 9 shows a proposed reaction mechanism for obtaining a compound (III) (Ar is C$_6$H$_5$), according to certain embodiments.
Figure 10A:
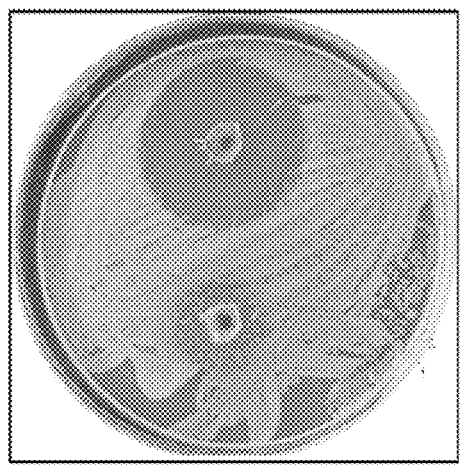
FIG. 10A is a Petri dish showing the inhibition zone of a compound (III) (Ar is 4-ClC$_6$H$_4$ and CH$_2$C$_6$H$_4$) against *Staphylococcus aureus*, according to certain embodiments.
Figure 10B:
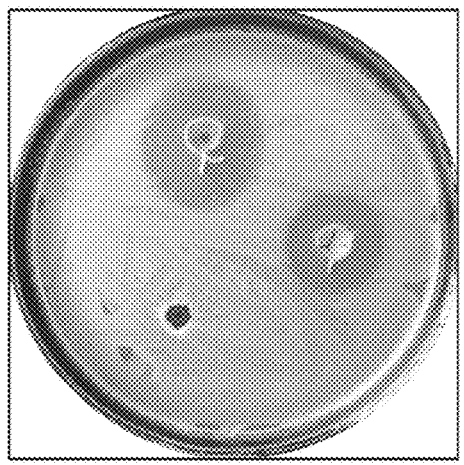
FIG. 10B is a Petri dish showing the inhibition zone of the compound (I), compound (II), and a compound (III) (Ar is C$_6$H$_5$) against *Staphylococcus aureus*, according to certain embodiments.
Figure 10C:
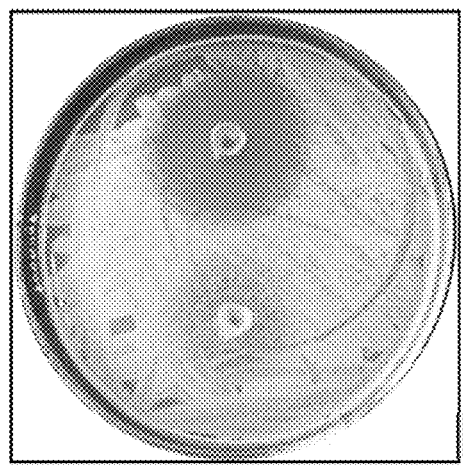
FIG. 10C is a Petri dish showing the inhibition zone of a compound (III) (Ar is 4-ClC$_6$H$_4$ and CH$_2$C$_6$H$_4$) against *Escherichia coli*, according to certain embodiments.
Figure 10D:
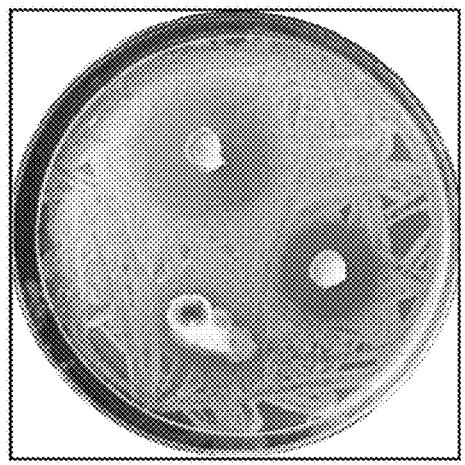
FIG. 10D is a Petri dish showing the inhibition zone of the compound (I), compound (II), and a compound (III) (Ar is C$_6$H$_5$) against *Escherichia coli*, according to certain embodiments.
Figure 11A:
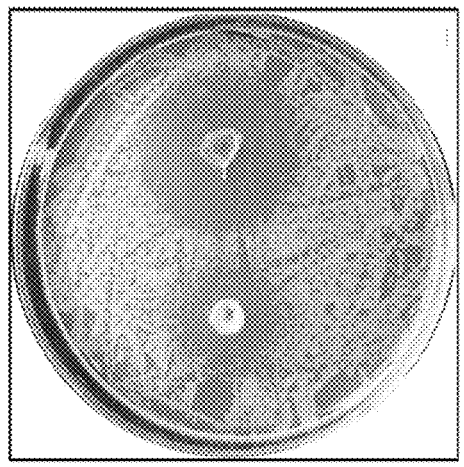
FIG. 11A is a Petri dish showing the inhibition zone of a compound (III) (Ar is 4-ClC$_6$H$_4$ and CH$_2$C$_6$H$_4$) against *Candida albicans*, according to certain embodiments.
Figure 11B:
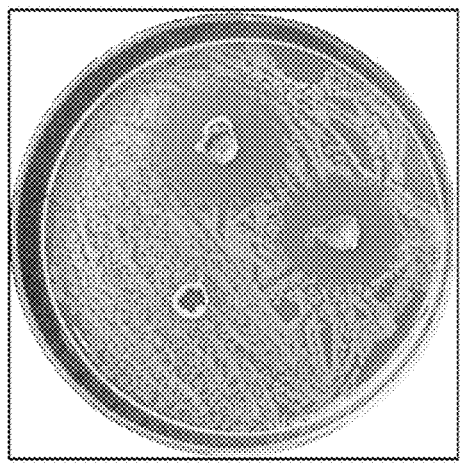
FIG. 11B is a Petri dish showing the inhibition zone of the compound (I), compound (II), and a compound (III) (Ar is C$_6$H$_5$) against *Candida albicans*, according to certain embodiments.
Figure 11C:
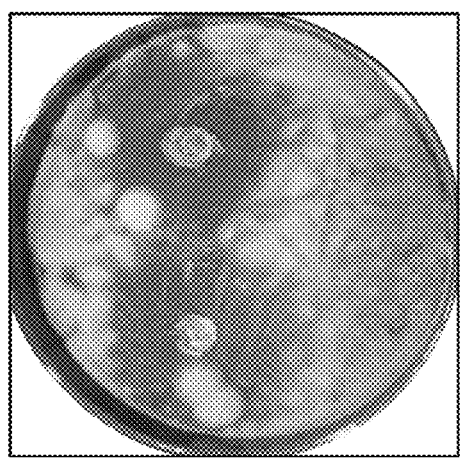
FIG. 11C is a Petri dish showing the inhibition zone of a compound (III) (Ar is 4-ClC$_6$H$_4$ and CH$_2$C$_6$H$_4$) against *Aspergillus niger*, according to certain embodiments.
Figure 11D:
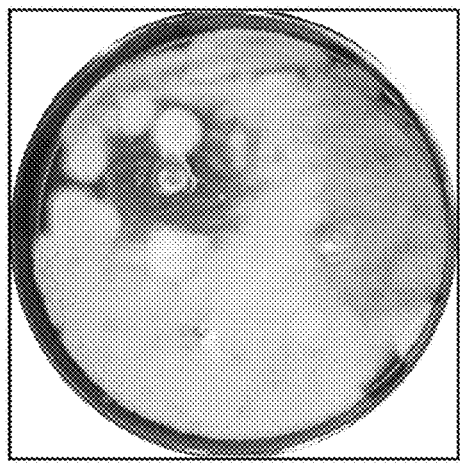
FIG. 11D is a Petri dish showing the inhibition zone of the compound (I), compound (II), and a compound (III) (Ar is C$_6$H$_5$) against *Aspergillus niger*, according to certain embodiments.

FIG. 7 depicts a reaction scheme for synthesizing thiazolidinone derivatives of Formula (II) (compound (III)) by reaction of compound (I) with N-aryl maleimides (N-phenylmaleimide, N-(4-chlorophenyl)maleimide, or N-benzylmaleimide) to yield 17-hydroxy-10,13-dimethyl-1,2,6,7,8,9,10,11,12,13,14,15,16,17-tetradecahydro-3H-cyclopentaphenanthren-3-ylidene) hydra zono)-4-oxothiazolidin-5-yl)-N-phenylacetamide, N-(4-chlorophenyl)-17-hydroxy-10,13-dimethyl-1,2,6,7,8,9,10,11,12,13,14,15,16,17-tetradecahydro-3H-cyclopenta[a]phenanthren-3-ylidene)hydrazono)-4-oxothiazol idin-5-yl)acetamide, or N-benzyl-17-hydroxy-10,13-dimethyl-1,2,6,7,8,9,10,11,12,13,14,15,16,17-tetradecahydro-3H-cyclopentaphenanthren-3-ylidene)hydrazono)-4-oxothiazolidin-5-yl)acetamide, corresponding to Ar=C$_6$H$_5$, 4-ClC$_6$H$_4$ or CH$_2$C$_6$H$_4$, respectively. The synthesis of thiazolidinone derivatives of Formula (II) was carried out by mixing a reaction mixture of compound (I) (0.1 g, 0.27 mmol) and N-aryl maleimides (N-phenylmaleimide, N-(4-chlorophenyl)maleimide, or N-benzylmaleimide) (0.27 mmol) in methanol (25 mL), in the presence of acetic acid. The reaction mixture was heated under reflux at 65° C. until TLC indicated completed consumption of compound (I) (6 to 9 h), then cooled overnight in a −20° C. freezer. The solids formed were filtered off, dried, and recrystallized from methanol to obtain the thiazolidinone derivatives of Formula (II) (FIG. 7). The estimated yield of the thiazolidinone derivatives of Formula (II) ranged from 74 to 89%; when Ar is C$_6$H$_5$, 4-ClC$_6$H$_4$, or CH$_2$C$_6$H$_4$, the corresponding yield is 74%, 85%, or 89%, respectively. Compound III where Ar is C$_6$H$_5$; (IR (KBr) v/cm$^{-1}$: 3314 (OH), 3062 (CH$_{aromatic}$), 2936 (CH$_{alkyl}$), 1718 (C=O), 1610 (C=N). $^1$H-NMR (400 MHz) DMSO-d$_6$, δ (ppm): 0.67 (3H, s, CH$_3$), 0.77-0.81 (1H, m, CH), 0.85 (2H, t, CH$_2$), 1.04 (3H, s, CH$_3$), 1.16-1.23 (2H, m, CH$_2$), 1.31 (1H, m, CH), 1.34-1.37 (2H, m, CH$_2$), 1.47-1.50 (2H, m, CH$_2$), 1.69-1.77 (2H, m, CH$_2$), 1.85-1.88 (2H, m, CH$_2$), 1.92 (1H, m, CH), 2.08-2.18 (2H, m, CH$_2$), 2.28-2.37 (2H, m, CH$_2$), 3.07 (2H, d, CH$_2$C=O) 3.16 (1H, t, CH), 4.34 (1H, t, CH—S—) 5.83 (1H, s, CH=), 7.05-7.58 (5H, m, C$_6$H$_5$), 10.10 (1H, s, NH-Ph), 11.78 (1H, br, NH—C=O) (FIG. 8).

Example 5: Antimicrobial Activity of the Synthesized Compounds

The antimicrobial activity of the synthesized testosterone-based thiazolidinone derivatives (compound (I), compound (II), and compound (III)) were assessed utilizing the disk diffusion agar methodology. Four representative microbial strains were selected for this study: *Staphylococcus aureus* ATCC 6538-P (Gram-positive), *Escherichia coli* ATCC 25933 (Gram-negative), *Candida albicans* ATCC 10231, and *Aspergillus niger* NRRL-A326. Nutrient agar plates were uniformly inoculated with 0.1 mL of a cell suspension at a density of 10' to 10$^6$ cells/mL for both bacterial and yeast cultures. Following inoculation, samples were introduced onto the agar plates. The plates were subsequently incubated at refrigeration temperature (4° C.) for 2 to 4 hours to enhance the diffusion of the antimicrobial agents. Thereafter, the plates were incubated at 37° C. for 24 hours for bacterial growth and at 30° C. for 48 hours for yeast and fungal growth, maintaining an upright orientation to maximize the growth of the microorganisms. The antimicrobial activity of the testosterone-based thiazolidinone derivatives was quantified by measuring the diameter of the zone of inhibition, which was reported in millimeters (mm). The concentration of the tested testosterone-based thiazolidinone derivatives was 25 mg/ml. This experimental protocol was replicated multiple times, and the mean values of the observed readings were recorded.

The findings in Table 1 indicate that the testosterone-based thiazolidinone derivatives exhibit antimicrobial activity against the microorganisms under investigation, particularly when compared to the baseline activity of testosterone thiosemicarbazone before any chemical modifications (compound (I)). Notably, the chemical modification of compound (I) resulted in an increased inhibitory effect against the tested bacterial and fungal species. (FIG. 10A to FIG. 10D and FIG. 11A to FIG. 11D)

TABLE 1

Diameter of inhibition zone (mm) of the tested compounds

| Compound No. | Bacterial and fungal growth inhibition zone diameter (mm) | | | |
| --- | --- | --- | --- | --- |
| | S. aureus | E. coli | C. albicans | A. niger |
| I | 0 | 0 | 0 | 0 |
| II | 29 | 26 | 29 | 0 |
| III Ar = $C_6H_5$ | 35 | 32 | 36 | 37 |
| Ar = 4-$ClC_6H_4$ | 38 | 39 | 41 | 43 |
| Ar = $CH_2C_6H_4$ | 19 | 17 | 21 | 44 |

Numerous modifications and variations of the present disclosure are possible in light of the above teachings. It is, therefore, to be understood that within the scope of the appended claims, the invention may be practiced otherwise than as specifically described herein.

The invention claimed is:

1. A method of synthesizing a testosterone-based thiazolidinone, comprising:
   preparing a testosterone thiosemicarbazone by reacting a thiosemicarbazide solution with a testosterone solution in an acidic medium while stirring at a temperature of 60 to 80° C. for 6 to 8 h; and
   reacting the testosterone thiosemicarbazone with a cyclization reagent in an organic solvent to obtain a testosterone-based thiazolidinone of Formula (I)

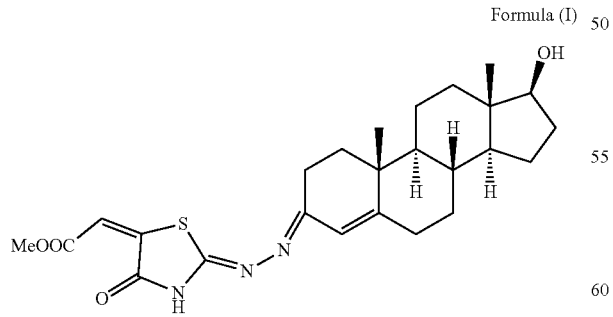

Formula (I)

wherein the thiosemicarbazide solution comprises a thiosemicarbazide dissolved in at least one selected from the group consisting of methanol, ethanol, isopropanol, propanol, acetone, ethylene glycol, glycerol, and tetrahydrofuran (THF).

2. The method of claim 1, wherein the thiosemicarbazide solution comprises at least one selected from the group consisting of methanol and ethanol.

3. The method of claim 1, wherein the acidic medium comprises at least one selected from the group consisting of acetic acid, citric acid, formic acid, oxalic acid, benzoic acid, carbonic acid, and phosphoric acid.

4. The method of claim 1, wherein the thiosemicarbazide solution comprises methanol.

5. The method of claim 1, wherein the thiosemicarbazide solution comprises ethanol.

6. The method of claim 1, wherein the acidic medium is acetic acid.

7. The method of claim 1, wherein the cyclization reagent is at least one selected from the group consisting of dimethyl acetylenedicarboxylate (DMAD), diethyl acetylenedicarboxylate (DEAD), di-tert-butyl acetylenedicarboxylate (DTBAD), and dibenzoyl acetylene (DBA).

8. The method of claim 1, further comprising:
   separating a testosterone thiosemicarbazone solution into a solid phase and a liquid phase; and
   drying the solid phase to obtain the testosterone thiosemicarbazone.

9. The method of claim 8, wherein the testosterone thiosemicarbazone solution has a molar ratio of testosterone to thiosemicarbazide of 1:5 to 5:1.

10. The method of claim 1, wherein the cyclization reagent is DMAD.

11. The method of claim 1, wherein the organic solvent is at least one selected from the group consisting of methanol, ethanol, isopropanol, propanol, acetone, ethylene glycol, glycerol, and THF.

12. The method of claim 1, wherein the organic solvent is acetone.

13. A method of synthesizing a testosterone-based thiazolidinone having antimicrobial activity, comprising:
   preparing a testosterone thiosemicarbazone by reacting a thiosemicarbazide solution with a testosterone solution; and
   reacting the testosterone thiosemicarbazone with an N-aryl maleimide in an organic solvent to obtain a testosterone-based thiazolidinone of Formula (II)

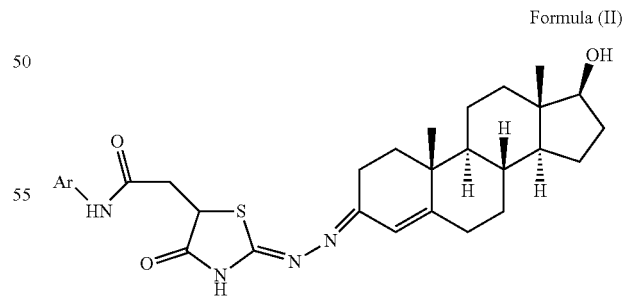

Formula (II)

wherein Ar is $C_6H_5$, 4-$ClC_6H_4$, and $C_6H_4$—$CH_2$.

14. The method of claim 13, wherein the N-aryl maleimide is N-phenylmaleimide and Ar is $C_6H_5$.

15. The method of claim 13, wherein the N-aryl maleimide is N-(4-chlorophenyl)maleimide and Ar is 4-$ClC_6H_4$.

16. The method of claim 13, wherein the N-aryl maleimide is N-benzylmaleimide and Ar is $C_6H_4$—$CH_2$.

17. The method of claim 13, wherein the organic solvent is acetone.

18. The method of claim 1, wherein the testosterone-based thiazolidinone has an inhibition zone diameter of at least 25 mm against at least one of a *Staphylococcus aureus* gram-positive bacterium and an *Escherichia coli* gram-negative bacterium.

19. The method of claim 13, wherein the testosterone-based thiazolidinone has an inhibition zone diameter of at least 15 mm against at least one of a *Staphylococcus aureus* gram-positive bacterium and an *Escherichia coli* gram-negative bacterium.

20. The method of claim 13, wherein the testosterone-based thiazolidinone has an inhibition zone diameter of at least 20 mm against at least one of a *Candida albicans* fungus and an *Aspergillus niger* fungus.

* * * * *